(12) United States Patent
Levien

(10) Patent No.: US 7,360,544 B2
(45) Date of Patent: Apr. 22, 2008

(54) INHIBITION ACTION INCONTINENCE DEVICE AND METHOD

(76) Inventor: David H. Levien, 82 Military St., Houlton, ME (US) 04730

( * ) Notice: Subject to any disclaimer, the term of this patent is extended or adjusted under 35 U.S.C. 154(b) by 253 days.

(21) Appl. No.: 10/951,709

(22) Filed: Sep. 29, 2004

(65) Prior Publication Data

US 2006/0069300 A1    Mar. 30, 2006

(51) Int. Cl.
*A61B 19/00* (2006.01)
*A61F 2/00* (2006.01)

(52) U.S. Cl. .......................... 128/897; 600/29

(58) Field of Classification Search ................ 128/897, 128/898, DIG. 25, 885, 887; 600/37, 29–32
See application file for complete search history.

(56) References Cited

U.S. PATENT DOCUMENTS

| | | | | |
|---|---|---|---|---|
| 2,615,445 | A | * 10/1952 | Holmes | 128/98.1 |
| 3,618,556 | A | * 11/1971 | Dittrich | 116/63 C |
| 4,484,919 | A | * 11/1984 | Sohn et al. | 604/358 |
| 4,686,985 | A | * 8/1987 | Lottick | 606/192 |
| 5,007,894 | A | * 4/1991 | Enhorning | 600/29 |
| 5,421,827 | A | 6/1995 | Temple | |
| 6,096,057 | A | 8/2000 | Klingenstein | |
| 6,464,628 | B1 | 10/2002 | Forsell | |
| 6,491,623 | B2 | 12/2002 | Snyder et al. | |
| 6,503,189 | B1 | 1/2003 | Forsell | |
| 6,508,794 | B1 | 1/2003 | Palumbo et al. | |
| 6,533,717 | B2 | 3/2003 | Silverman et al. | |
| 6,547,773 | B2 | 4/2003 | Kleinschmidt et al. | |

OTHER PUBLICATIONS

David Levien et al, "Manometric Study of the Voluntary Inhibitiion Action in Normal Volunteers," Dis Colon Rectum, Aug. 1994, vol. 37, No. 8, pp. 770-774.

Levien et al.; Manometric Study of the Voluntary Inhibition Action in Normal Volunteers; From the Departments of Surgery, Episcopal Hospital and The Medical College of Pennsylvania, Philadelphia, Pennsylvania and Division of Gastroenterology at New York Medical College, Valballa, New York; Dis Colon Rectum; Aug. 1994.

* cited by examiner

*Primary Examiner*—Samuel G Gilbert
(74) *Attorney, Agent, or Firm*—Blank Rome LLP

(57) ABSTRACT

A method and apparatus for minimizing fecal incontinence in a subject, is disclosed. An inhibition action incontinence device includes a truncated cone with an angled concavity at a top portion. The truncated cone is positioned at the external opening of the anal canal. The truncated cone may be positioned to effect a positive pressure on the external sphincter muscles and the anal slit across the peri-anal tissues. It is believed that the truncated cone exploits the voluntary inhibition action of the external sphincter muscles and the simple mechanical closure of the anal slit to decrease fecal incontinence and soiling.

11 Claims, 2 Drawing Sheets

INHIBITION ACTION INCONTINENCE DEVICE AND METHOD

FIELD OF THE INVENTION

The present invention is generally related to fecal incontinence and, more particularly, is related to a method and apparatus for minimizing fecal incontinence.

BACKGROUND OF THE INVENTION

Fecal incontinence is described as the loss of the normal control of the bowels. This leads to stool leaking from the rectum at unexpected times. Fecal incontinence typically is a source of physical discomfort and the cause of social and personal debilitation. It most often affects the aged or individuals suffering from neurological, obstetrical, or other traumatic injury. However, abnormalities in stool volume or consistency, colonic transit, anal sphincter function, anal rectal sensation, cerebral function and anal rectal reflexes also may result in incontinence. A significant number of incontinence cases involve postpartum pelvic neuropathies, and thus, may affect women at a relatively young age.

There may be many causes of fecal incontinence. Fecal continence is multi-faceted. Anal sphincter resting and squeeze pressure, rectal storage capacity, anal and rectal sensation, spinal reflexes, cognition, and anorectal angle all play a role. The anal sphincter is a muscle that contracts to prevent stool from leaving the rectum. That muscle is critical in maintaining continence. The rectum can stretch and hold stool for some time after a person becomes aware that stool is there. That is the rectal storage capacity. Rectal sensation tells a person that stool is in the rectum. Then, the person knows that it is time to go to the bathroom. A person also must be alert enough to notice the rectal sensation and do something about it. He or she must be able to move to a toilet. If something is wrong with any of these factors, then fecal incontinence can occur.

Fecal incontinence may also be caused by a reduction in the compliance of the rectum, which shortens the time between the sensation of the stool and the urgent need to have a bowel movement. Surgery or radiation injury can scar and stiffen the rectum. Inflammatory bowel disease can also make the rectum less compliant.

Because loose stool (diarrhea) is more difficult to control than formed stool, diarrhea is an added stress that can lead to fecal incontinence. A change in stool consistency to a looser form often causes the problem of incontinence to become manifest.

Some cases of fecal incontinence are treated by instituting dietary changes, providing anti-diarrheal agents, fiber exploiting the gastro-colic reflex Not eating prior to attending an important engagement), and effecting "pseudo-continence" by emptying the distal colon and rectum with enemas prior to social events. Biofeedback therapies also have been proposed in which a balloon, inserted in the rectum, provides a sensation similar to that of stool immediately prior to defecating. The patient is trained to perceive differing volumes of distention in the balloon and to respond accordingly by contracting the anal sphincter muscles.

Surgical remedies for severe cases of fecal incontinence include sphincter repair, plication of the posterior sphincter, anal encirclement in which a metal or elastic band mechanically tightens the anus, and muscle transfer procedures. Each of those techniques attempts to create a mechanical barrier to stool. Anal sphincter repair may produce good results, but it is appropriate for women with obstetric injuries to the anal sphincter, and may be effective to a lesser extent for those with other traumatic sphincter injuries. Those patients, though not target subjects for the present invention, could benefit from this invention if surgery is unsuccessful due to concomitant pudendal nerve injury, or if they are poor operative candidates because of their generally poor health, or if they do not want to submit to an invasive procedure. Other surgical procedures typically produce suboptimal results because of persistent leakage of stool, infection and fecal impaction.

Temple, U.S. Pat. No. 5,421,827, discloses an incontinence device that includes a generally tubular soft latex shape that is opened at both ends. The upper end is smoothly curved and tapered inward to the opening with latex of minimal thickness and coated on the outside adjacent the opening with a suitable adhesive for contact with the skin about the anal opening. However, the device is invasive, blocks the anal opening and collects fecal matter and gases in the tubular shape provided.

Klingenstein, U.S. Pat. No. 6,096,057, discloses a fecal incontinence device and method that includes an expandable tubular member that invasively is inserted into the rectum of a patient. The tubular member has attached thereto a pair of bilaterally extending wings which may be detachable that conform to the surface of the buttocks of a patient, thereby maintaining the position of the device in the rectum. A sheath is expanded so as to prevent passage of stool through the anal opening, but cannot be expanded to such an extent as to trigger a defecation reflex.

A problem with such non-surgical devices for controlling fecal incontinence is that they are intrusive or invasive. Accordingly, there is a need in the art for a means for controlling fecal incontinence that is convenient and non-invasive.

SUMMARY OF THE INVENTION

Embodiments of the present invention provide an apparatus and method for minimizing fecal incontinence in a patient.

Briefly described, one embodiment of the system, among others, can be implemented as follows. In a preferred embodiment, the claimed invention exploits the voluntary inhibition action and/or simple mechanical closure of the anal slit to decrease fecal incontinence or soiling. The present invention includes a truncated cone located at an external aspect of the anal canal. The truncated cone includes a concavity on a top portion to effect an inward positive pressure on the external sphincter muscles and the anal slit. The truncated cone could be made of silicone or other comparable material, a synthetic skin or envelope filled with a fluid, air or other comparable gas. The efficacy of the invention is predicated on exploiting the voluntary inhibition action whereby contraction of the external sphincter muscles causes a reflex relaxation of the rectum, thus increasing the rectum's reservoir capacity and decreasing the need to defecate. The invention may also act by simply closing the anal slit. In the preferred embodiment, the present invention is comprised of silicone plastic. The invention may be used multiple times or, may be disposable. The invention could also be utilized with a disposable or reusable covering.

Embodiments of the present invention can also be used as providing methods for minimizing fecal incontinence. In that regard, a preferred embodiment of such a method, among others, can be broadly summarized by the following steps. An inhibition action incontinence device is positioned at the external opening of the anal canal of a subject. The inhibition action incontinence device effects a positive pressure on the external sphincter muscles and the anal slit by virtue of an inward vector applied across the peri-anal tissues. The device is non-invasive and does not require insertion into the anal canal.

In another embodiment of the invention, the inhibition action incontinence device includes positioning a balloon in the rectum and inflating the balloon via air, water or other comparable void-filling liquid or gas to anchor the device so that it may apply positive pressure on the external sphincter muscles across the peri-anal tissues. This embodiment, though minimally invasive, could allow utilization of the device in ambulatory patients.

In still another embodiment of the invention, the inhibition action incontinence device includes an envelope that can be filled with varying amounts of water, air or other comparable void-filling liquid or gas to produce the positive pressure that effects the external sphincter muscles.

The inhibition action incontinence device may be used while the subject is sitting, standing, or in a supine position. A channel may be located in a top portion of the truncated cone or the envelope for developmental medical procedures. The channel may traverse from the top to the bottom of the truncated cone and the envelope. Such developmental medical procedures may include anorectal manometry to determine the optimal shape of the truncated cone to maximize the salutary effect on rectal compliance and the anal slit. A therapeutic use of the channel could be for the administration of enemas to facilitate defecation at a time convenient for the patient, or for the staff should the patient be institutionalized.

Other systems, methods, features, and advantages of the present invention will become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components of the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENT

Figure 1:
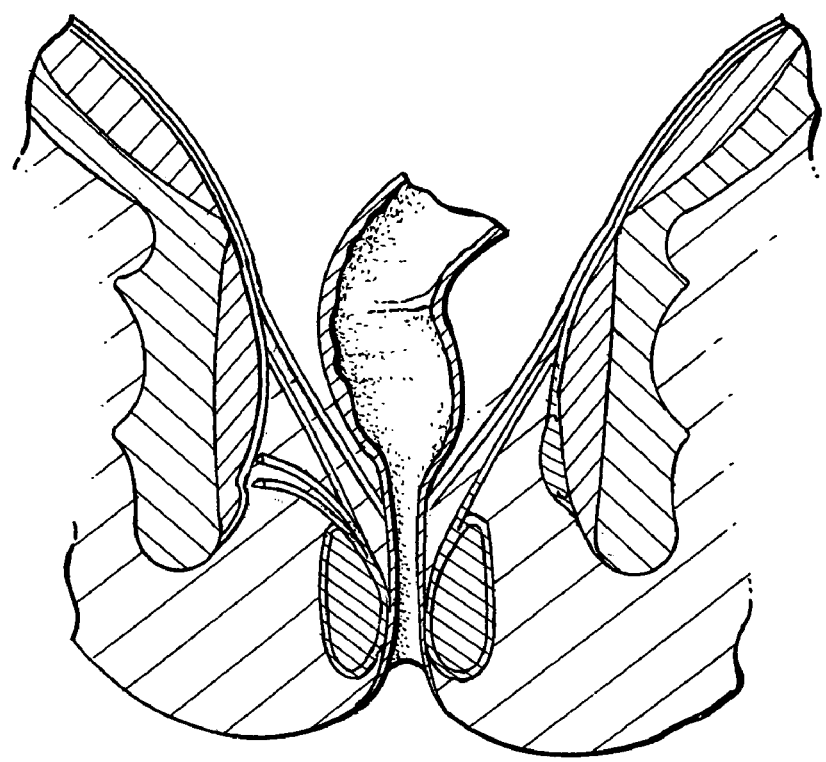
FIG. 1 is a schematic drawing of a frontal section of the rectum, pelvic diaphragm and anal canal.

FIG. 1 illustrates a frontal section of the rectum, pelvic diaphragm and anal canal. It is believed that a voluntary inhibition action exists whereby a voluntary squeeze of the external sphincter muscles causes a reflex relaxation of the rectum. Such a reflex could enable a subject to defer defecation until a more socially acceptable time by causing the rectum to increase its compliance to accommodate a fecal bolus.

Figure 2:
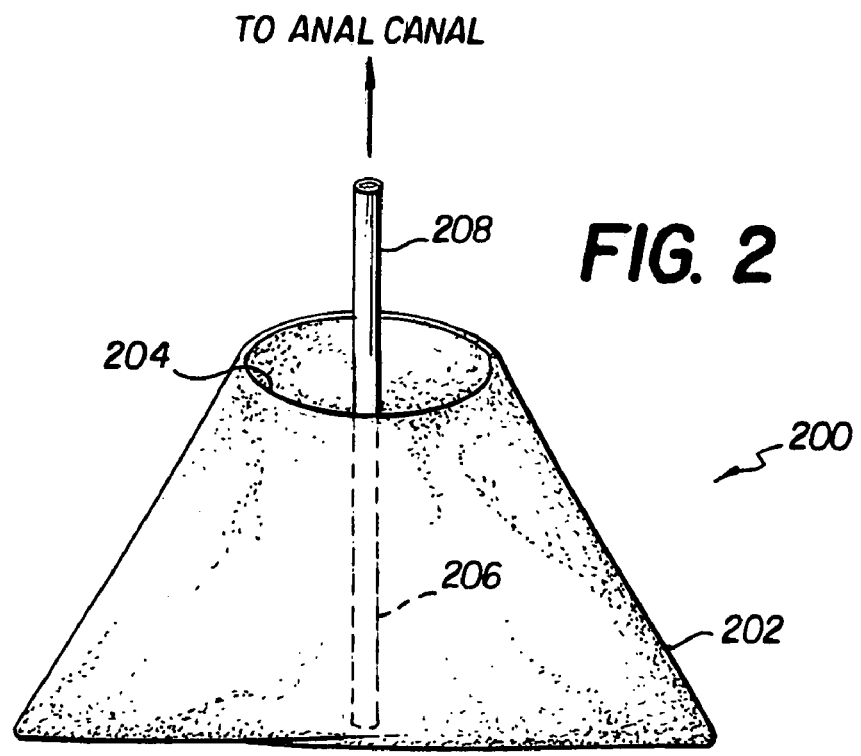
FIG. 2 is a perspective drawing of a preferred embodiment of the invention with the optional channel and catheter.

In FIG. 2, a preferred embodiment of an inhibition action incontinence device is shown. The inhibition action incontinence device 200 includes a truncated cone 202 with an angled concavity 204 at a top portion. The truncated cone 202 may be positioned at or near the external opening of the anal canal. The truncated cone 202 will exert its effect across the peri-anal tissues to effect a positive pressure on the external sphincter muscles and the anal slit. By effecting a positive inward pressure on the external sphincter muscles, it is believed that the truncated cone 202 causes a reflex action in the rectum to relax the rectum and enlarge the rectum's capacity. A channel 206 may traverse the truncated cone 202 from top to bottom for insertion of a manometry catheter 208 or enema tube(not shown) or other such catheters for further developmental medical and therapeutic procedures. In the preferred embodiment, the truncated cone 202 is composed of silicone plastic.

Figure 3:
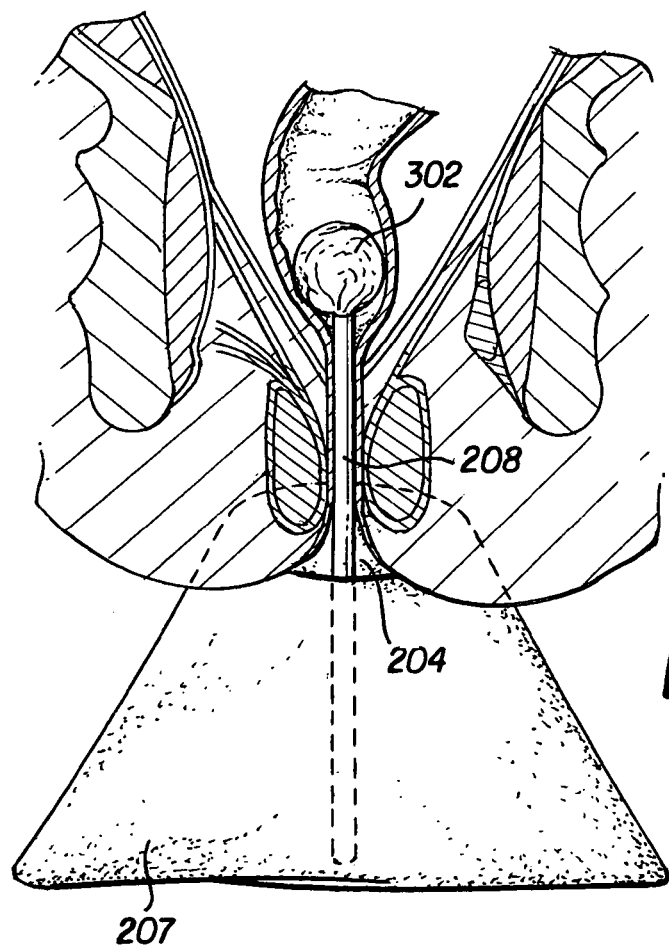
FIG. 3 is a perspective drawing of a second embodiment of the invention.

FIG. 3 illustrates another embodiment of the claimed invention. In FIG. 3, the truncated cone 202 includes a balloon 302 that is disposed in the rectum. The balloon is positioned above the anorectal ring and may be inflated via the catheter 208 that leads from the truncated cone 202 to the rectum. Varying amounts of water, air or other comparable void-filling gas or liquid may be used to inflate the balloon 302. As described above, the pressure of the balloon anchors the truncated cone 202 so that the truncated cone 202 may exert its effect on the external and internal sphincter and anal slit across the peri-anal tissues.

Figure 4:
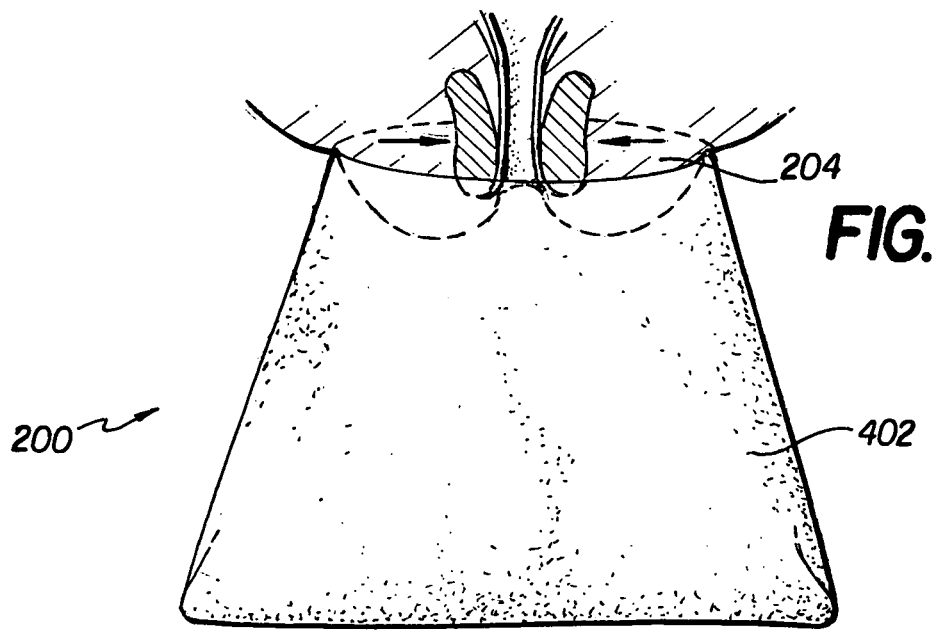
FIG. 4 is a perspective drawing of a third embodiment of the invention.

FIG. 4 illustrates yet another embodiment of the claimed invention. In FIG. 4, the truncated cone 202 includes a doughnut-shaped envelope 402. The doughnut-shaped envelope 402 may be filled with varying amounts of air, water or other comparable void-filling gas or liquid. The degree of air or water is dependent upon the effective pressure that is needed to produce a positive inward pressure on the external sphincter muscles and the anal slit. Hence, the degree or amount of water or air may vary dependent upon the subject.

It is proffered that the inhibition action incontinence device 202 may be used while a subject is seated on a chair, lying in a supine position, or strapped to the subject while in a standing position.

It should be emphasized that the above-described embodiments of the present invention, particularly, any preferred embodiments, are merely possible examples of implementations, merely set forth for a clear understanding of the principles of the invention. Many variations and modifications may be made to the above-described embodiments of the invention without departing substantially from the spirit and principles of the invention. All such modifications in variations are intended to be included herein within the scope of this disclosure and the present invention and protected by the following claims.

What is claimed is:

1. A method for minimizing fecal incontinence in a subject, comprising:

positioning a cone-shaped inhibition action incontinence device exteriorly near the external opening of the anal canal of the subject; and non-invasively exerting a positive pressure on the anal sphincter muscles and the anal slit across the peri-anal tissues of the subject using the device to cause contraction of the anal sphincter muscle and reflexive relaxation of the rectum.

2. The method according to claim 1, wherein relaxation of the rectum increases the reservoir function of the rectum.

3. The method according to claim 1, further comprising using the device in a seated position.

4. The method according to claim 1, further comprising using the device in a supine position whereby the subject is on top of the inhibition action incontinence device which is positioned proximate the peri-anal tissues, and non-invasively across the peri-anal tissues.

5. The method according to claim 1, further comprising using the device in a standing position by strapping the device to the subject.

6. The method according to claim 5, further comprising positioning a balloon in the rectum and inflating the balloon to anchor the inhibition action incontinence device in a manner to apply across the peri-anal tissues positive pressure on the external sphincter muscles from outside the anus.

7. The method according to claim 1, wherein the inhibition action incontinence device includes a truncated cone with an angled concavity at a top portion.

8. The method according to claim 7, wherein the inhibition action incontinence device further includes a channel extending from the top to the bottom of the truncated cone to accommodate various catheters.

9. An inhibition action incontinence device, comprising:

a truncated cone comprising a doughnut-shaped envelope adapted to being filled with an amount of fluid sufficient to provide, when the truncated cone is positioned proximate the external opening of the anal canal of a subject, a positive inward pressure on the external and internal sphincter muscles to cause contraction of the sphincter muscles and reflexive relaxation of the rectum.

10. The device of claim 9, wherein the fluid is one of air and water.

11. A method for minimizing fecal incontinence in a subject, comprising:

positioning a cone-shaped inhibition action incontinence device exteriorly across the peri-anal tissues near the external opening of the anal canal of the subject; and non-invasively exerting a positive pressure on the anal sphincter muscles and the anal slit using the device to cause contraction of the anal sphincter muscle and closing of the anal slit.

* * * * *